US010994115B2

(12) United States Patent
Peer et al.

(10) Patent No.: US 10,994,115 B2
(45) Date of Patent: May 4, 2021

(54) LUER CONNECTOR WITH ON-BOARD CONNECTION INDICATOR

(71) Applicant: ORIDION MEDICAL 1987 LTD., Jerusalem (IL)

(72) Inventors: Roni Peer, Yehud (IL); Noam Erlich, Naan (IL); Avi Finkelstein, Zur Igal (IL); Alon Sasson, Rehovot (IL); Ori Porat, D.N. Hof Ashkelon (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 1487 days.

(21) Appl. No.: 15/019,897

(22) Filed: Feb. 9, 2016

(65) Prior Publication Data

US 2017/0224975 A1 Aug. 10, 2017

(51) Int. Cl.
*H01R 4/60* (2006.01)
*A61M 39/10* (2006.01)

(52) U.S. Cl.
CPC ........ *A61M 39/10* (2013.01); *A61M 39/1011* (2013.01); *A61M 2039/1027* (2013.01); *A61M 2039/1033* (2013.01); *A61M 2039/1044* (2013.01); *A61M 2039/1083* (2013.01); *A61M 2039/1088* (2013.01); *A61M 2205/18* (2013.01); *A61M 2205/581* (2013.01); *A61M 2205/582* (2013.01); *A61M 2205/583* (2013.01); *A61M 2205/60* (2013.01)

(58) Field of Classification Search
CPC .............. A61M 39/10; A61M 39/1011; A61M 2039/1027; A61M 2039/1033; A61M 2039/1044; A61M 2039/1083; A61M 2039/1088; A61M 2205/18; A61M 2205/581; A61M 2205/582; A61M 2205/583; A61M 2205/60
USPC ........................................................ 439/191
See application file for complete search history.

(56) References Cited

U.S. PATENT DOCUMENTS

| 4,834,706 A | * | 5/1989 | Beck | ................... A61M 39/1011 604/111 |
| 4,925,444 A | * | 5/1990 | Orkin | ................ A61M 5/16827 123/DIG. 13 |
| 5,405,269 A | * | 4/1995 | Stupecky | ............... A61B 5/087 439/191 |

(Continued)

*Primary Examiner* — Abdullah A Riyami
*Assistant Examiner* — Vladimir Imas
(74) *Attorney, Agent, or Firm* — Cantor Colburn LLP

(57) ABSTRACT

A connector connection indicator is mounted in a Luer male connector, or in a Luer female connector, to indicate proper mating of the two Luer connectors. The connection indicator may be or include a light source, a sound producing device (e.g., buzzer), a switch, a tactile connection indicator or an electronic chip. The electronic chip may be interposed between two conductive elements that are mounted in the Luer female connector. When the two Luer connectors are properly engaged, the electronic chip is powered via two electrical terminals. While the electronic chip is powered up it communicates with an external system via two electrical terminals. The external system interprets the communication with the electronic chip as an indication to proper engagement of the two Luer connectors. Some of the connection indicators may be mounted on a circuit board that is embedded in a void in the Luer male connector.

25 Claims, 10 Drawing Sheets

(56) References Cited

U.S. PATENT DOCUMENTS

| | | | | |
|---|---|---|---|---|
| 5,690,612 A * | 11/1997 | Lopez | A61M 5/14 | 604/246 |
| 5,822,137 A * | 10/1998 | Abul-Haj | G02B 7/00 | 359/808 |
| 5,997,818 A * | 12/1999 | Hacker | G01N 21/05 | 210/232 |
| 6,009,339 A * | 12/1999 | Bentsen | G01N 21/05 | 600/322 |
| 6,200,293 B1 * | 3/2001 | Kriesel | A61M 5/14248 | 128/DIG. 12 |
| 6,437,316 B1 * | 8/2002 | Colman | A61M 39/10 | 250/222.1 |
| 6,768,425 B2 * | 7/2004 | Flaherty | A61B 5/14532 | 128/920 |
| 7,377,553 B2 * | 5/2008 | Takayanagi | F16L 37/0987 | 285/307 |
| 7,377,915 B2 * | 5/2008 | Rasmussen | A61M 25/0097 | 604/523 |
| 7,488,229 B2 * | 2/2009 | Ben-Oren | A61B 5/083 | 313/573 |
| 7,591,181 B2 * | 9/2009 | Ales | G01N 29/043 | 73/597 |
| 7,976,532 B2 * | 7/2011 | Kitani | A61M 39/26 | 604/533 |
| 8,180,093 B2 * | 5/2012 | Hankey | H04R 1/083 | 381/374 |
| 8,414,542 B2 * | 4/2013 | Stroup | A61M 5/16881 | 604/246 |
| 8,733,349 B2 * | 5/2014 | Bath | A61M 16/0066 | 128/204.17 |
| 8,746,745 B2 * | 6/2014 | Colman | A61M 39/1011 | 285/93 |
| 8,758,306 B2 * | 6/2014 | Lopez | A61M 39/16 | 604/247 |
| 8,905,985 B2 * | 12/2014 | Allen | A61F 13/00068 | 604/319 |
| 8,956,519 B2 * | 2/2015 | Leonard | G01N 27/4167 | 204/416 |
| 9,149,623 B1 * | 10/2015 | Colman | F16L 25/01 | |
| 9,218,556 B2 * | 12/2015 | Colman | G06K 19/06046 | |
| 9,592,353 B2 * | 3/2017 | Roy | A61M 5/5086 | |
| 9,713,417 B2 * | 7/2017 | Levy | A61B 1/00096 | |
| 9,907,943 B2 * | 3/2018 | Grant | A61M 5/14586 | |
| 10,112,024 B2 * | 10/2018 | Geraghty | A61M 16/0486 | |
| 10,493,262 B2 * | 12/2019 | Tran | A61M 39/24 | |
| 10,561,440 B2 * | 2/2020 | Look | A61B 17/22 | |
| 2006/0271015 A1 * | 11/2006 | Mantell | A61M 13/003 | 604/533 |
| 2017/0224975 A1 * | 8/2017 | Peer | A61M 39/10 | |

* cited by examiner

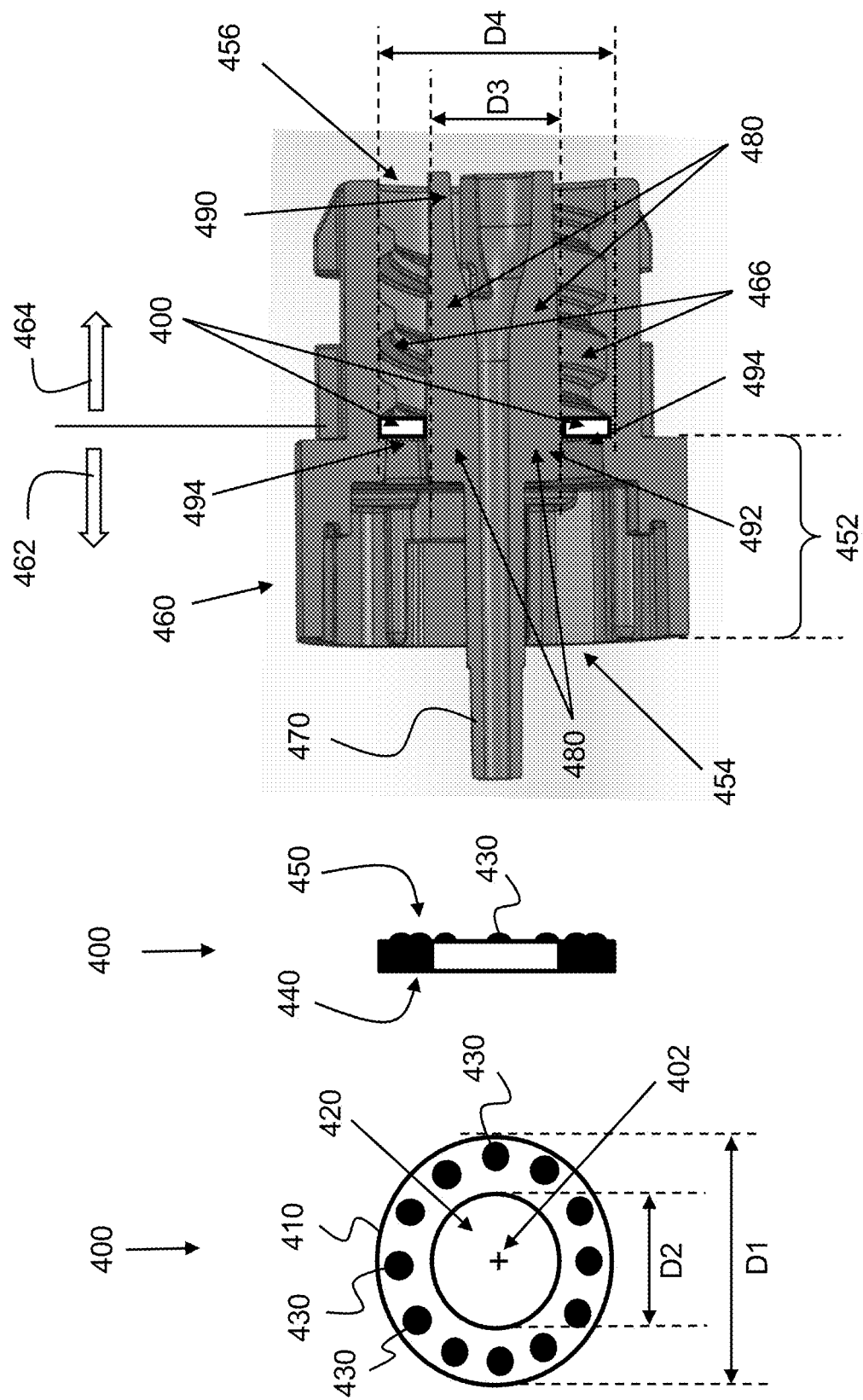

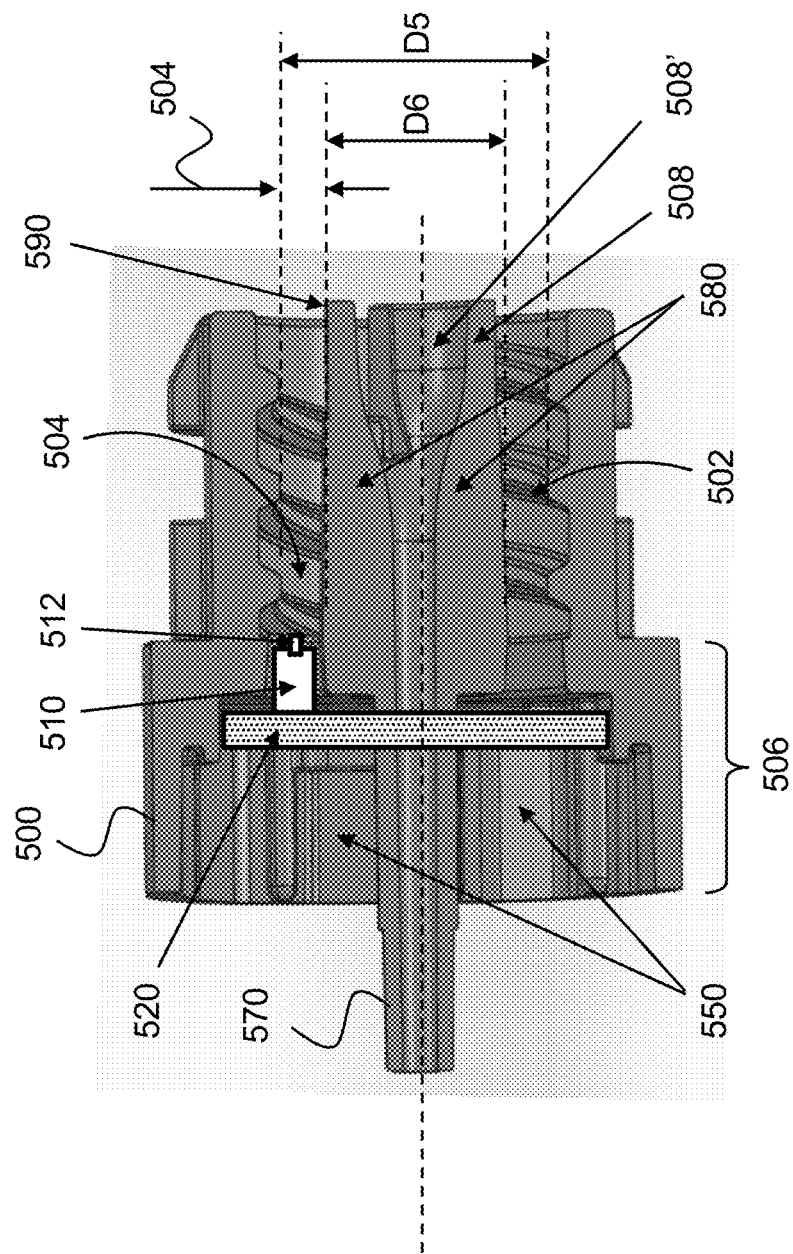

LUER CONNECTOR WITH ON-BOARD CONNECTION INDICATOR

FIELD OF THE INVENTION

The present invention relates to tubing connectors in general, and, in particular, to Luer connectors.

BACKGROUND

The Luer Taper is a standardized system of small-scale tubing fittings used for making leak-free connections between a male-taper fitting and a mating female part/fitting on medical and laboratory instruments. Luer Taper connectors are defined in, for example, the ISO 594 standards and other standard. One type of Luer connectors is called "Luer-Lock". In general, Luer-Lock fittings are securely joined by screwing a 'male' thread on the periphery of a female fitting into a 'female' thread in a sleeve of the male fitting. Luer connectors are manufactured from metal or plastic, and are widely used, for example, in the medical field. Example Luer-Lock connectors are shown in FIGS. 1A-1C, which is described below.

FIG. 1A shows a cross-sectional view of an example Luer connector system 100. Luer connector system 100 includes a primary Luer male connector 102 and a primary Luer female connector 104. Primary Luer male connector 102 includes a female part (a void) 106 that forms a secondary female section having a conical shape 107 that extends from a distal part 108 of primary Luer male connector 102 back into primary Luer male connector 102 towards the proximal part thereof. Primary Luer male connector 102 includes a (centralized) first inner fluid flow channel 110 that extends along (passes through) its length from the proximal end of primary Luer male connector 102 to (and in fluid flow connection with) secondary female section 106. First inner flow channel 110 has a diameter of dl. At a connection point of/between first inner fluid flow channel 110 and secondary female section 106 the internal diameter is increased to form a neck (N) having a diameter that is greater than dl.

On the mating connector, in primary Luer female connector 104, which is primarily female in shape and includes an external screwing thread 122, a tapered conical part inverts back into the void space 114 of primary Luer female connector 104 to form a secondary male section 116, which has a conical shape. A second inner fluid flow channel 118, which extends along and through secondary male section 116, also has a diameter dl.

Primary Luer male connector 102 and primary Luer female connector 104 mate such that inadvertent insertion of a larger male Luer connector into a smaller female Luer connector is prevented as required by the standard(s). It is noted that, for simplicity, the 'main' parts of the male and female Luer connectors are respectively referred to herein as the 'primary male connector' and the 'primary female connector', and the inverted sections (i.e., female void 106 in the primary male connector, and conical protrusion 116 in the primary female connector) are respectively referred to herein as the 'secondary female section' and the 'secondary male section'. (The secondary female section is concentrically formed inside the connector's male part 102, and the secondary male section is concentrically formed inside the connector's female part 104.)

Secondary male section 116 and secondary female section 106 have tapered angles whose tolerances are on the lower side of the tapered angle of primary Luer male connector 102 and primary Luer female connector 104. The tolerances are selected such that the two fittings do not close first on the (shorter and smaller) secondary male and female sections, but, rather, mate primarily with the primary male and female cones.

An outer section of Luer connector system 100 further includes screwing capability of one connector to its mating connector: primary Luer male connector 102 includes an 'inner' thread 120 on an outer part thereof, and primary Luer female connector 104 includes a thread 122 on an outer part thereof. When primary Luer male connector 102 and primary Luer female connector 104 mate with each other, secondary male section 116 is at least partially inserted into (mate with) secondary female section 106.

FIGS. 1B-1C respectively show isometric view of an example male Luer connector 130 and an example female Luer connector 140. Male Luer connector 130 includes a primary male connector 132. Female Luer connector 140 includes a primary female connector 142. Primary male connector 132 and primary female connector 142 are engaged (150) by screwing 'female' threads 144 into 'male' threads 134 using male lock 136 and female lock 146.

Primary male connector 132 includes a secondary female section, and primary female connector 142 includes a secondary male section that is inserted into the secondary female section of primary male connector 132 when primary male connector 132 and primary female connector 142 are engaged.

For various reasons (e.g., gas measurement accuracy), it would have been beneficial to identify proper mating of a Luer male connector and a Luer female connector.

SUMMARY

It would, therefore, be beneficial to provide an indication as to whether the male part and female part of a Luer connector are properly engaged, for example during a medical procedure.

A Luer connector system is provided, which includes a Luer male connector suitable for a Luer female connector. The Luer male connector may include a connector base and a base void (350) formed in the connector base. The Luer male connector may include a primary male member that extends distally, in a first direction, from the connector base, and the primary male member may include a concentric secondary female member that may have a female void. The Luer male connector may also include a first elongated electrical terminal and a second elongated electrical terminal that extend along a length of the Luer male connector, and a connection indicator. The first and second elongated electrical terminals may be configured to electrically attach to a conductive element that is mounted on a secondary male member of a Luer female connector in order to power up the connection indicator to indicate when the Luer male connector and the Luer female connector mate properly.

The Luer male connector may include the connection indicator, which may be or include a device selected from the group consisting of: a light source, a sound making device (e.g., buzzer) and an electromechanical vibrator. The light source may be optically coupled to an optical fiber via which a user may see a light that originates from the light source. Alternatively or additionally, the Luer male connector may include an optical window through which light originating from the light source may be visible to the user. The connection indicator may reside in the base void of the Luer male connector.

The base void may include a circuit board, and the first elongated electrical terminal, second elongated electrical terminal and the connection indicator may be mounted on, or otherwise electrically connected to, the circuit board. Each of the first and second electrical terminals has a proximal end and a distal end, each proximal end is mounted on the circuit board and each distal end extends in the first direction into the female void of the secondary female member, and the connection indicator is electromechanically configured such that it can be powered up ('turned on', activated) via the circuit board, via the first and second electrical terminals, and via the conductive element, which are mounted on the secondary male member of the Luer female connector, when the Luer male connector and the Luer female connector mate properly. The circuit board may be ring shaped in order to enable through-passage of a connector tube. The first and second electrical terminals may be pre-conditioned to flex by the conductive element mounted on the secondary male member of the Luer female connector when the Luer male connector and the Luer female connector mate properly.

The conductive element mounted on the secondary male member may include two conductive rings that may be axially spaced apart along a length of the secondary male member. Each of the first and second electrical terminals may be configured to flexibly contact a different one of the two conductive rings when the Luer male connector and the Luer female connector mate properly.

The connection indicator may be or may reside in an electrical circuit that may be interposed between the two conductive rings, and may be powered via the two conductive rings and via the first and second electrical terminals when the Luer male connector and the Luer female connector properly mate. The electrical circuit may include a controller, a communication interface and a memory. The controller may send data to, and/or to receive data from, an external system (e.g., medical system; e.g., capnography system) via the communication interface when the Luer male connector and the Luer female connector properly mate. The controller may communicate with the external system via the two conductive rings and via the first and second elongated electrical terminals. The data that is exchanged between the controller and the external system may be selected from the group consisting of: (i) data related to an identification (ID) of a tube connected to the Luer male connector, (ii) data related to the Luer male connector or to a system that can use the tube or Luer connector system, (iii) data related to a class or type of the tube that is in use, (iv) data related to a number of times that the tube was used, and (v) data related to an accumulated time that the tube was in use. The external system may detect proper mating of the Luer male connector and the Luer female connector through, by or using communication with the controller. The base void of or in the Luer male connector may include the circuit board and a second connection indicator that may be mounted on the circuit board, and the external system may output a connection indication signal to the second connection indicator when the external system detects proper mating of the Luer male connector and the Luer female connector through.

A Luer female connector connectable to the Luer male connector is also provided. The Luer female connector may include a primary female member to mate with a primary male member of the Luer male connector, and a secondary male member to mate with a secondary female member of the Luer male connector. The secondary male member is concentrically formed in the primary female member. The Luer female connector may also include two conductive elements that are axially spaced apart on the secondary male member along a lengthwise axis of the secondary male connector. The Luer female connector may also include an electrical circuit that is interposed between the two conductive elements. The electrical circuit may be electrically powered via the two conductive elements (rings) when the Luer female connector and the Luer male connector mate properly.

The electrical circuit may include a controller, a communication interface and a memory, and the controller may communicate with an external system via the two conductive elements on the secondary male member when the Luer female connector and the Luer male connector properly mate.

In another embodiment, a Luer male connector including a rounded tactile connection indicator is provided. The Luer male connector may include a screwing thread and a primary male member extending distally from a connector base of the Luer male connector. The primary male member may be internally concentric to the screwing thread. The Luer male connector may contain a flat, rounded, tactile connection indicator that is mounted between the screwing thread and the primary male member. The flat tactile connection indicator may have a first side and a second side that has a friction surface. The first side and the friction surface of the flat connection indicator may respectively face a tube insertion opening and a Luer female connector insertion opening of the Luer male connector.

The flat connection indicator may include (e.g., it may have formed on the friction side) a plurality of convex projections that are configured to respectively occupy a plurality of concave recesses in a primary female member of a Luer female connector when the Luer male connector and the Luer female connector mate properly. A tactile indication indicating (e.g., to a user) proper mating of the Luer male connector and the Luer female connector is indicated when the plurality of convex friction projections respectively occupy the plurality of concave recesses. In some embodiments the convex projections may be evenly spaced around a center point of the rounded tactile connection indicator. In other embodiments the convex projections may be unevenly spaced around the center point of the rounded tactile connection indicator.

In another embodiment, a Luer male connector including a switch as the connection indicator is provided. Luer male connector may include a connector base including a base void, a circuit board that resides in the base void, a screwing thread to facilitate mating with a Luer female connector, a primary male member extending distally from the connector base and internally concentric to the screwing thread, and a switch. The circuit board may be ring shaped to enable through-passage of a tube.

The switch may be mounted on the circuit board and reside between the screwing thread and the primary male member. The switch is configured to transition from an 'open' state of the switch to a 'closed' state of the switch when the Luer male connector and the Luer female connector mate properly. The switch may include a pin plunger that is actuatable by a primary female member of the Luer female connector, to thereby transition the switch to the 'closed' state in which the switch outputs an electrical signal indicative of proper mating of the Luer male connector and the Luer female connector.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 4A-4B respectively show a front view and side view of a ring-shaped tactile indicator according to an example embodiment;

FIG. 4C depicts a Luer male connector including the ring-shaped tactile indicator of FIGS. 4A-4B; and FIG. 5 shows a cross-sectional view of a Luer connector including a micro switch in accordance with another example embodiment.

DETAILED DESCRIPTION OF THE INVENTION

The description that follows provides various details of exemplary embodiments. However, this description is not intended to limit the scope of the claims but, instead, to explain various principles of the invention and the manner of practicing it.

In the following description, various embodiments and aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The Luer connectors disclosed herein have embedded therein an electrical component (which is referred to herein as a 'connector-mating indicator' ("CMI") and a 'connection indicator', the two terms being used interchangeably) that, when activated, produces an indication signal (e.g., light, sound, tactile, etc.), for example for a healthcare personnel, that the Luer male and female connectors involved are properly mated. The CMI may be embedded or incorporated in the Luer male connector or in the Luer female connector, or partly in the Luer male connector and partly in the Luer female connector. The CMI in the Luer connector, and the Luer connector itself, are designed such that the CMI can be activated only when the Luer male connector and the Luer female connector are properly mated or engaged. (The term "Luer connector", as used herein, refers to a pair, or connector 'set', including a Luer male connector and a Luer female connector.)

Figure 1A:
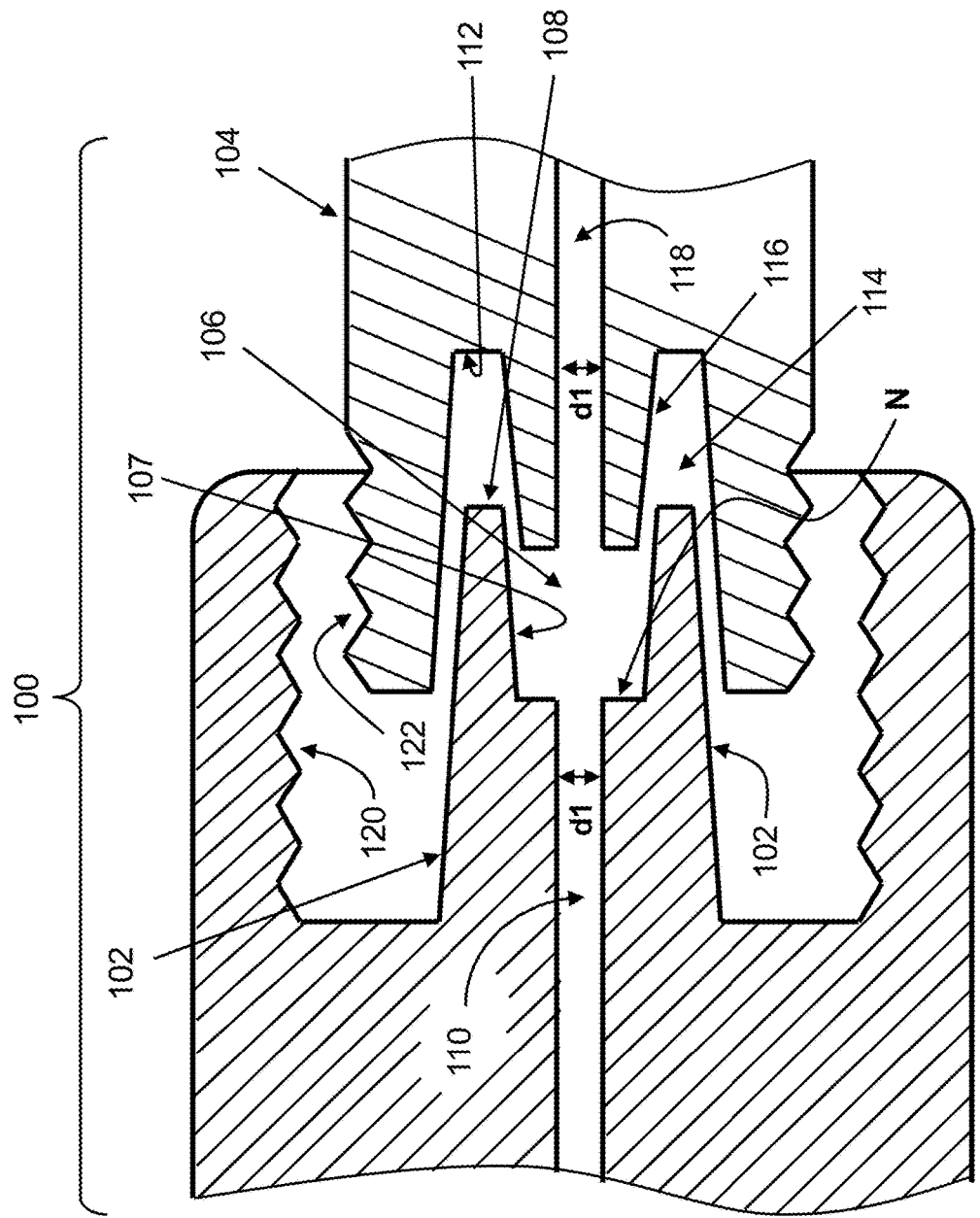
FIG. 1A (prior art) schematically illustrates a cross-sectional view of an example Luer connector.
Figures 1B, 1C:
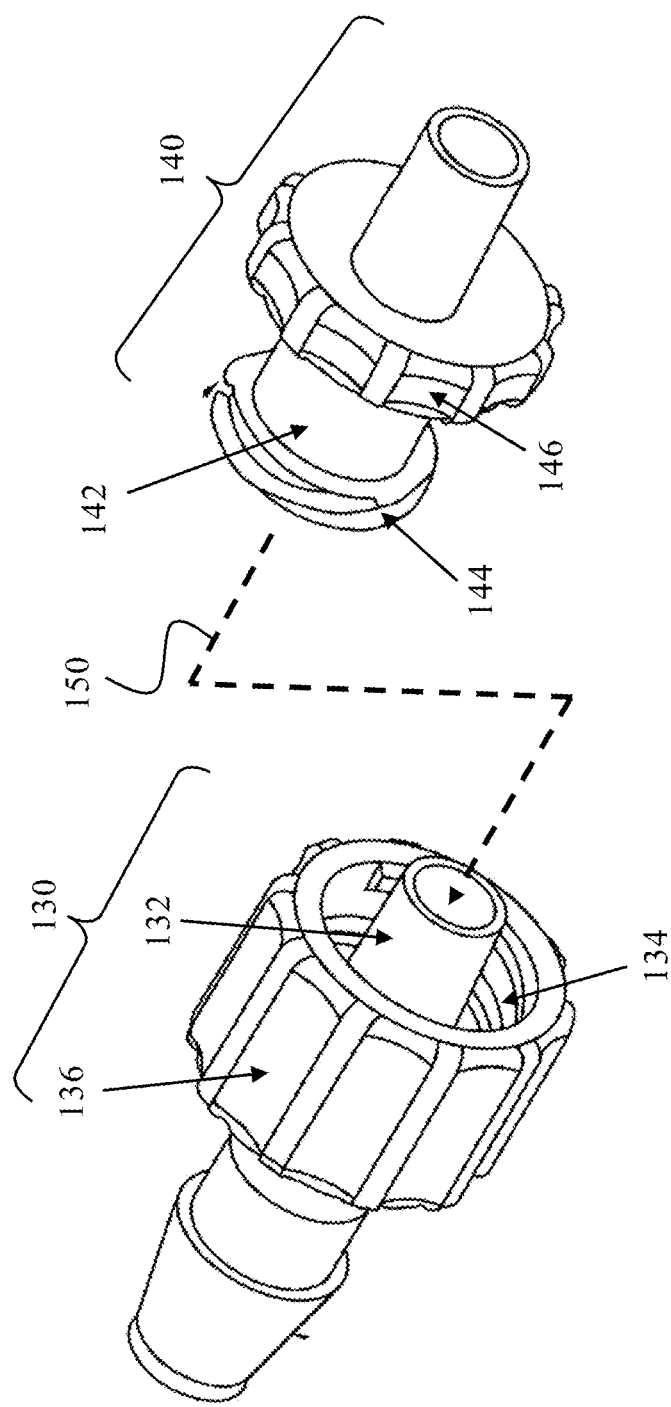
FIGS. 1B-1C (prior art) respectively show isometric view of example male Luer connector and a matching female Luer connector.
Figure 2A:
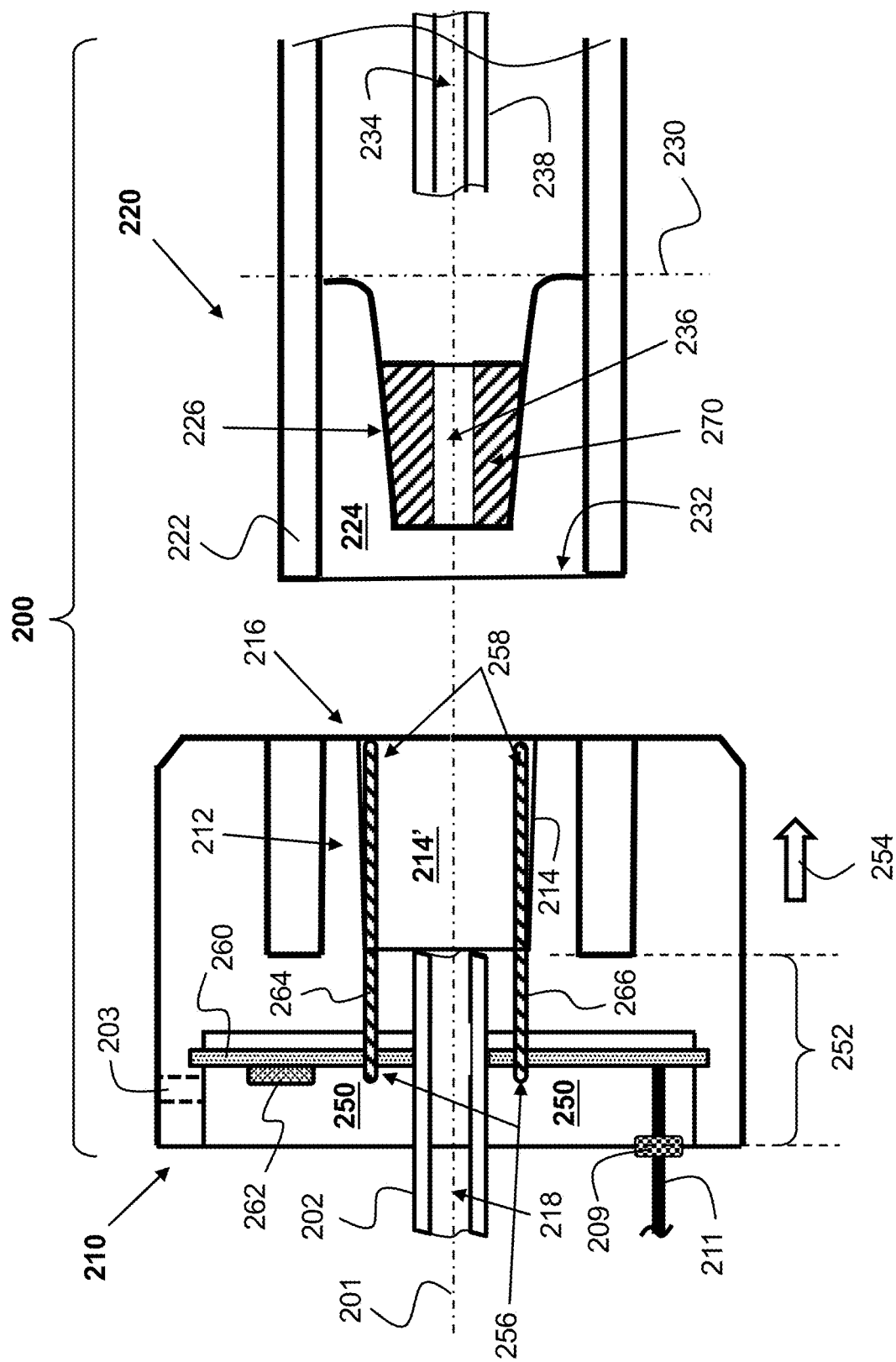
FIG. 2A schematically illustrates a cross-sectional view of a one-ring Luer connector according to an example embodiment.

FIG. 2A schematically illustrates a cross-sectional view of a Luer connector system 200 according to an example 'one-ring' embodiment. Luer connector system 200 includes a Luer male connector 210 and a Luer female connector 220. (Connectors 210 and 220 are not necessarily drawn to scale.) Luer male connector 210 may include a primary Luer male member 212 and an inner concentric secondary Luer female member 214 having a female void 214'. Secondary Luer female member 214 concentrically resides or contained, or formed, in primary Luer male member 212. Luer male connector 210 includes a connector base 252. Primary Luer male member 212 extends forwardly, away (in a first direction designated as direction 254), from base 252 of Luer male connector 210. Primary Luer male member 212 (and Luer male connector 210 in general) has a longitudinal axis 201.

Primary Luer male member 212 may have a conical shape that extends from a distal part 216 of primary Luer male member 212 and 'folded' back into primary Luer male member 212. Luer male connector 210 may include a centralized first inner fluid flow channel 218 that may pass through a first tube 202 that may be connected, on the opposite end, to, for example, an external monitoring system (for example a medical analyzer). Tube 202 may extend along and pass through the length from a proximal end of primary Luer male member 212 to (and be in fluid flow connection with) void 214'. Luer male connector 210 has a screwing thread, though it is not shown in FIG. 2A.

On the mating 'side', Luer female connector 220 includes a primary Luer female member 222 and an inner concentric secondary Luer male member 226. Secondary Luer male member 226 concentrically resides or contained in primary Luer female member 222. Primary Luer female member 222 has a void 224. Secondary Luer male member 226 may extend or protrude in or into void 224 of primary Luer female member 222, for example from a male 'base' 230 towards a distal end 232 of primary Luer female member 222. Secondary Luer male part 226 may include, for example, an inner fluid flow channel 236. Fluid flow channel 236 may form, with fluid flow channel 218 (via female void 214) and a fluid flow channel 234 passing through a second tube 238 a continuous flow fluid channel. Luer connector system 200 may include a screwing mechanism for screwing Luer male connector 210 to Luer female connector 220. (To simplify FIG. 2A, the screwing threads enabling the screwing capability are not shown.)

Luer male connector 210 may include a base void, niche or recess 250 for accommodating (including or containing) a circuit board (e.g., printed circuit board—"PCB") 260. On circuit board 260 may be mounted a 'connector-mating' indicator (CMI) (also referred to herein as a 'connection indicator') 262 and electrical wiring to operate CMI 262 and, in some embodiments, to communicate with an external system, for example with an external monitoring system.

Circuit board 260 may be configured to receive an electric power from an external system (e.g., from a medical monitoring system), and to be in electrical communication with connection indicator 262. Connection indicator 262 may indicate, or provide indication, for example to a user (e.g., to a medical staff), that (or when) primary Luer male member 212 and primary Luer female member 222 properly mate with one another. The indication provided by connection indicator 262 may be selected from the group consisting of: a visual indication (e.g., by using a light source), an audible indication (e.g., by using a buzzer) and a tactile indication (e.g., by using an electric vibrator).

CMI 262 may be or include, or it may operate in conjunction with, a light source (e.g., light emitting diode (LED)) to produce, to a user, a visible connector connection indication, a micro switch that may output an indication signal or activate an indication producing device on board the Luer male connector and/or send an indication signal to an external system, a buzzer (or any other a sound making device) and/or an electromechanical vibrator that may be activated, for example, by the switch, a tactile signal/sensing generating device that outputs a tactile signal that can be sensed by the user rotating a Luer female connector into a Luer male connector, and the like. Light source 262 may be optically coupled to an optical fiber (not shown in FIG. 2A) via which a user may see a light that originates from the light source. Alternatively or additionally, Luer male connector 210 may include an optical window 203 (an indication or observation window) through which light originating from light source 362 may be visible to the user.

CMI 262 may be configured to produce an on-board 'perceptible signal' (e.g., light signal, audio signal, vibration signal, tactile signal, etc.) that can be sensed directly, for example by a healthcare person or technician. Alternatively or additionally, CMI 262 may be configured to produce and to send an electronic signal to an external system as an indication that Luer male connector 210 and Luer female connector 220 are properly engaged. CMI 262 may be powered (receive electrical power) by an external system. CMI 262 is activated (e.g., to produce the 'mating' indication) only when Luer male connector 210 and Luer female connector 220 mate/engage properly; that is, only when and so long as secondary Luer male member 226, in primary Luer female member 222, properly mates or engages with secondary Luer female member 214 in primary Luer male member 212.

Circuit board 260 may be, for example, ring shaped (e.g., it may be rounded with concentric through hole 268) to enable insertion there through (274) of tube 202 into Luer male connector 210 through circuit board 260 (e.g., during assembly of Luer male connector 210). Circuit board 260 may include CMI 262 and/or a micro switch. CMI 262 and the micro switch may be one device or separate devices.

A first electrical terminal 264 and a second electrical terminal 266 may each have a proximal end 256 that is mounted on circuit board 260, and a distal end 258 that extends forward (in direction 254), away from circuit board 260 and into female void 214' of secondary Luer female member 214. (Terminal 264 and terminal 266 may each be or include, for example, a flexible, or spring like, strip or pin, a wire, and the like.) Each of electrical terminals 264 and 266 may extend in, and along the length of, Luer male connector 210, for example in parallel with respect to a lengthwise axis 201 of Luer male connector 210. (Electrical terminals 264 and 266 may widen a bit; e.g., a few degrees, relative to axis 201, to match the cone shape of secondary Luer male connector 226.)

One of electrical terminals 264 and 266 (e.g., terminal 264) may be used as a positive voltage ("+V") terminal, and the other terminal (e.g., terminal 266) may be used as a negative voltage ("−V"), or as a "ground" ("Gnd."), terminal. Electrical terminals 264 and 266 may be configured to close an electrical circuit with a conductive element (e.g., one ring or two rings) that is mounted on secondary male member 226 of Luer female connector 220, to activate a connection indicator (e.g., CIM 262 or electronic chip 305) to provide indication that, or when, primary Luer male member 212 and primary Luer female member 222 properly mate with one another. The conductive element mounted on the secondary male member (e.g., on secondary male member 226 of Luer female connector 220, or on secondary male member 326 of Luer female connector 320 in FIG. 3A) may include one conductive ring (270), as demonstrated by, for example, FIG. 2A, or two, axially spaced apart, electrically conductive elements (e.g., electrically conducting rings 370 and 380), as demonstrated by, for example, FIG. 3A.

For example, electrical terminals 264 and 266 may extend from circuit board 260 such that, upon proper mating of, or engagement between, Luer male connector 210 and Luer female connector 220, both terminals 264 and 266 touch a conductive element (e.g., ring) 270. Each of electrical terminal 264 (a first terminal) and electrical terminal 266 (a second electrical terminal) may be configured to flexibly contact conductive ring 270 when Luer male connector 210 and Luer female connector 220 mate properly. That is, terminals 264 and 266 may be pre-conditioned to flex, or to deflect, in order for them to apply a spring like force on conductive ring 270 in order to ensure good electrical contact between each of terminals 264 and 266 and ring 270.

Terminals 264 and 266 are part of the electrical wiring of CMI 262. When Luer male connector 210 and Luer female connector 220 mate properly, the electrical circuit including, among other things, CMI 262 and terminals 264 and 266 is closed via ring 270, and CMI 262 is activated to produce a connector-mating indication or signal. Terminals 264 and 266 may have the same length, though they may differ in length provided that both terminals can still touch ring 270 when the Luer male and female connectors (210, 220) are properly engaged.

Luer male connector 210 may include an electrical connector or socket 209 to which an electrical cable 211 may be connected, via which circuit board 260 may receive electric power from an external system. The electrical schematic associated with Luer connector system 200 is described below in connection with, for example, FIG. 2B.

Figure 2B:
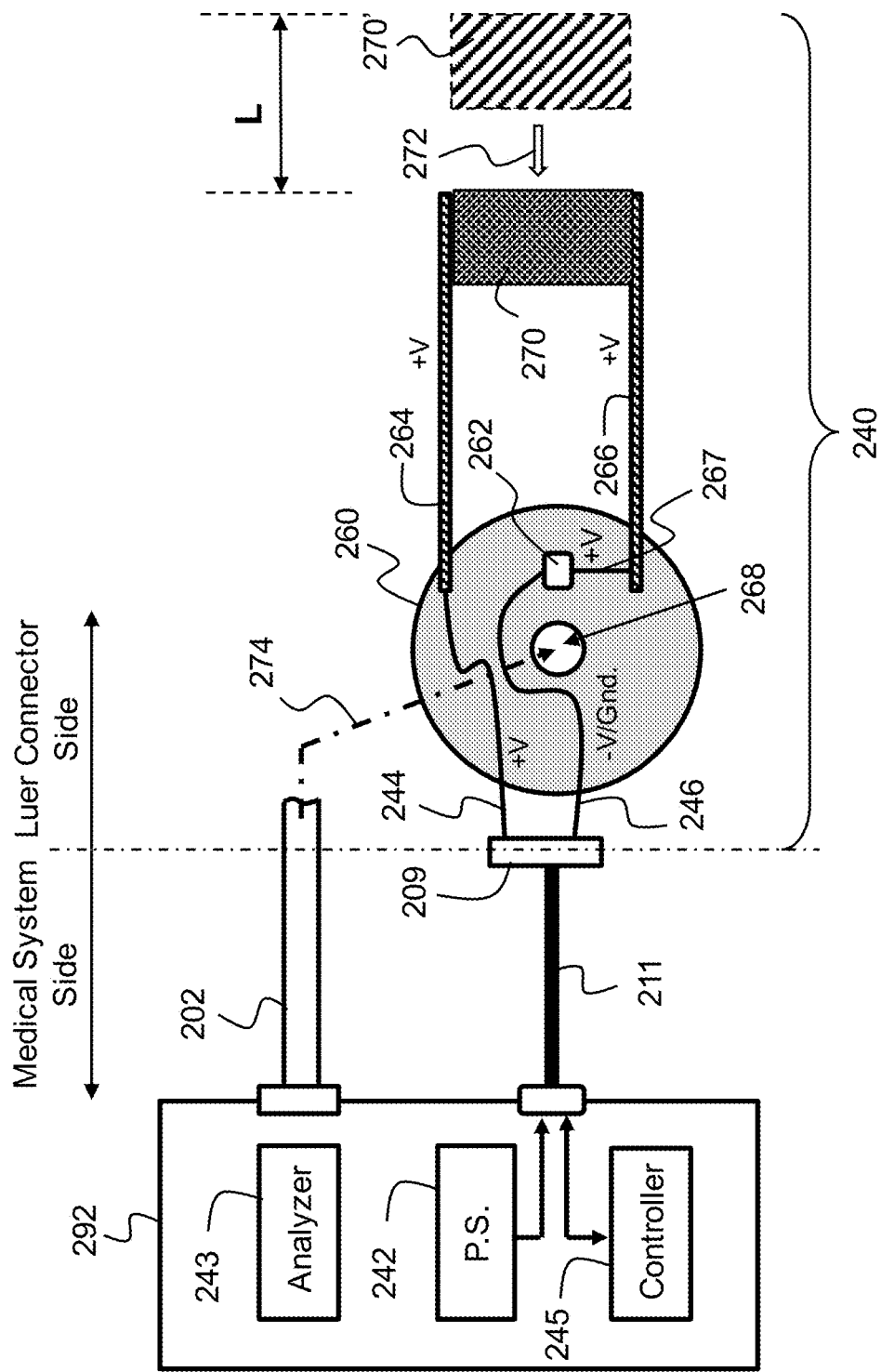
FIG. 2B schematically illustrates an example electrical circuit schematics of a one-ring Luer connector according to an example embodiment.

FIG. 2B schematically illustrates an electrical circuit 240 associated with (representing) Luer connector system 200 of FIG. 2A. Luer connector system 200 of FIG. 2A may be connected to a medical system 292 via flexible tube 202, and be electrically connected to medical system 292 via electrical cable 211.

Cable 211 is connected to a connector 209 on-board Luer male connector 210 (FIG. 2A), and it may contain power supply wires (not shown in FIG. 2B). The power supply wires, which may originate, and connected to, a power supply unit 242 of medical system 292, may respectively be electrically connected, via wires 244 and 246 and via a circuit board 260, to terminal 264, which may be used, for example, as a '+V' terminal, and to a power supply terminal (e.g., '−V/Gnd.') of a connection-monitoring indicator (CMI) 262.

When Luer male connector 210 and Luer female connector 220 are not engaged, conducting ring 270 (which is mounted on Luer female connector 220) does not touch terminal 264 and/or terminal 266 (which are both mounted on Luer male connector 210). (Conducting ring 270 is shown at 270', where it has a disengagement gap L at the Luer connector's disengagement state.) Therefore, the '+V' terminal of CMI 262 is disconnected from the '+V' voltage, thus CMI 262 is inactive.

During mating of Luer male connector 210 and Luer female connector 220, a disengagement' gap (L) exists between the Luer male and female connectors, but it narrows down as the two connectors near proper mating. When the Luer male connector and the Luer female connector are properly engaged (that is, when ring 270 is moved a distance L in direction 272 so that the value of L is zeroed out), both terminals 264 and 266 are connected to conducting ring 270. As a result of the connection between terminals 264 and 266 and ring 270, power supply 242 powers up CMI 262 by using an electrical path via cable 211, wire 244, terminal 264, ring 270 and terminal 266 and wire 267. (CMI 262 receives the power supply '−V/Gnd.' potential via wire 246 independently of ring 270.)

When CMI 262 is electrically powered, it may output an indication signal to indicate, for example to the system operator or user (e.g., healthcare person), that the Luer connector is properly connected. When the system operator or user get the indication that CMI 262 outputs, s/he can manually activate an analyzer 243 of system 292 to commence a medical procedure. For example, s/he can activate a pump in order for analyzer 243 to receive gas samples, for example exhaled carbon dioxide, via tube 202, and operate analyzer 243 to analyze or monitor an inflow gas.

In some embodiments, CMI 262 may be or include an electrical 'bridge' that electrically connects terminal 266 and wire 246 (via, e.g., wire 267). In these embodiments, medical system 292 may include a controller 245. Controller 245 may send a 'monitoring' or 'ping'-like signal via cable 211 and wire 244 (or via another wire) and sense the signal, as feedback signal, via wire 246 (or via another wire). When the male and female connectors are properly engaged, an electrical circuit including, among other things, a wire in cable 211, wire 244, terminal 264, ring 270 and terminal 266 is closed, and the monitoring signal sent by controller 245, for example via wire 244 (or via another wire), returns to controller 245, as feedback, via terminal 266, wire 267, bridge 262 (or a bridge in device 262), wire 246 (or another wire) and a wire in cable 211 selected for that purpose.

In response to receiving the feedback signal, controller 245 may respond by outputting, for example, an indication signal (e.g., visible, audible, tactile, etc.) to indicate (e.g., to the system operator, healthcare person or technician), that the two Luer connectors are properly mated. Controller 245 may output the indication signal by using a device on-board system 292. Alternatively or additionally, controller 245 may send a user-feedback signal to a CMI mounted on circuit board 260, for example via cable 211 and suitable wiring on circuit board 260, that is mounted on circuit board 260 to indicate proper mating of the Luer male and Luer female connectors. The CMI may be or include, for example, a light source, a buzzer, a vibrator, etc. A CMI mounted on circuit board 260 may be activated 'internally' (e.g., directly, that is, via the ring), or 'externally' (e.g., indirectly, by the medical system). (The terms 'internally' and 'externally' are used with respect to the Luer connector.)

Figure 3A:
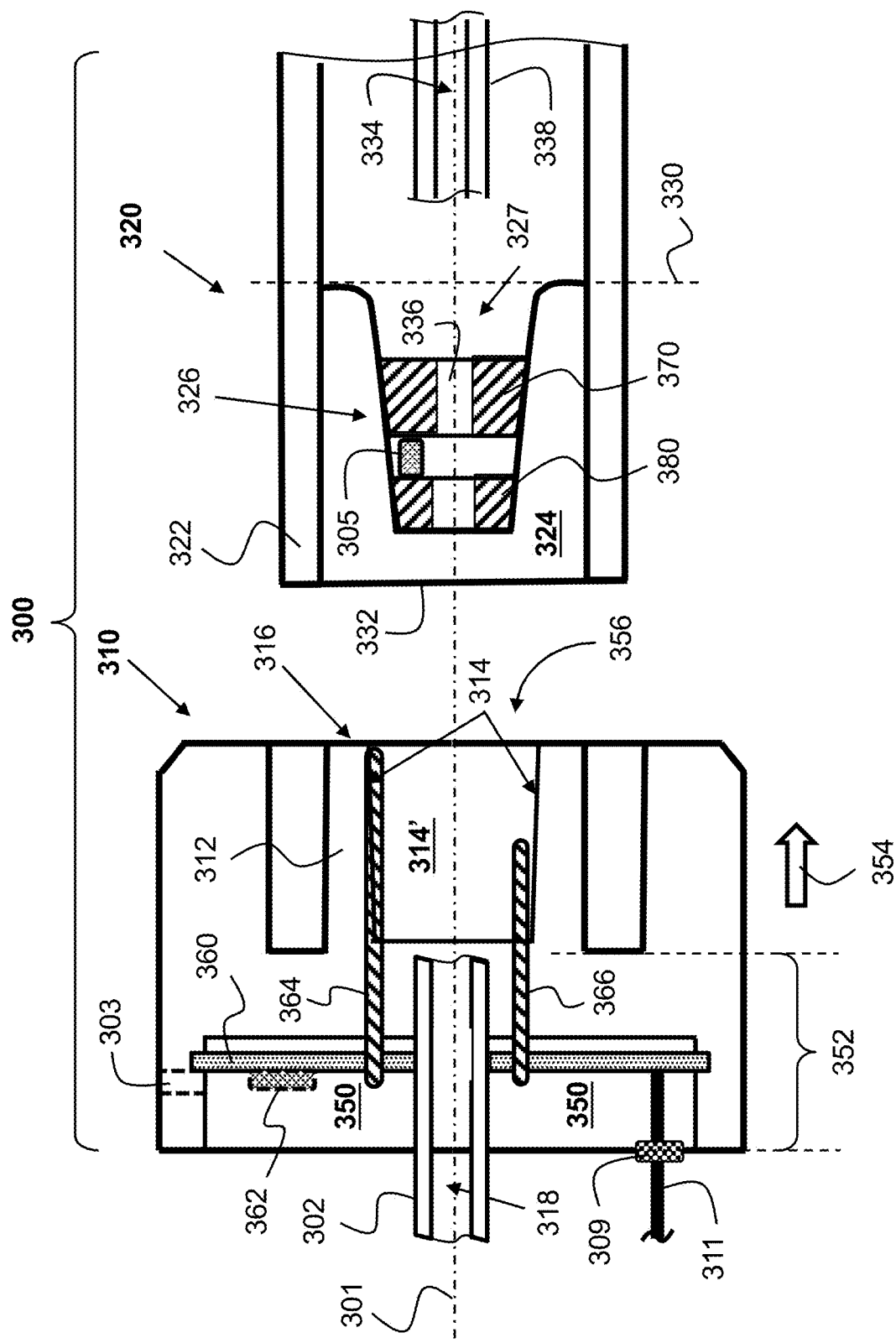
FIG. 3A schematically illustrates a cross-sectional view of a two-ring Luer connector according to an example embodiment.

FIG. 3A schematically illustrates a cross-sectional view of a Luer connector 300 according to another example embodiment. Luer connector 300 may include a Luer male connector 310 (a Filter Line Receptacle, or "FLR") and a Luer female connector 320 (a Filter Line Connector, or "FLC"). Luer male connector 310 (FLR) has a primary male member 312 that includes an inner concentrically secondary female member 314 with a void 314'. Luer male connector 310 includes a connector base 352, and primary male member 312 extends distally (in a first direction 354) from base 352, towards a Luer female connector insertion opening 356 of Luer male connector 310.

Luer female connector 320 has a primary female member 322 that includes an inner concentrically secondary male member 326. Primary male member 312 and primary female member 322 have a screwing mechanism and are engageable using the screwing mechanism. Secondary male member 326 is inserted into (engages with) secondary female member 314 when the primary male member (312) and the primary female member (322) are engaged.

Secondary male member 326 may extend or protrude into a void 324 of primary female member 322, for example from a base line 330 of secondary male member 326 towards a distal end 332 of primary female member 322. Secondary female member (void) 314 may have a conical shape that extends from a distal edge or base line 316 of primary male member 312 and 'folds' back into primary male member 312.

Luer male connector 310 and Luer female connector 320 may respectively be structured in a similar way as Luer male connector 210 and Luer female connector 220 of FIG. 2A except that, in the configuration of FIG. 3A, the conductive element of Luer female connector 320 includes two, axially spaced apart, conductive elements; e.g., rings 370 and 380, that are disposed along a lengthwise axis 301 of Luer female connector 320, and, in addition, two, elongated, electrical terminals (364,366) in Luer male connector 310 that have different lengths such that they are respectively configured to contact the conductive elements (e.g., ring 370 (a proximal ring) and ring 380 (a distal ring)) when the male and female connectors are properly engaged. (With respect to proximal ring 370 and distal ring 380, the terms 'proximal' and 'distal' denote the rings' relative location along the lengthwise axis 301, with the ring closest to base line 330 of secondary male member 326 (ring 370) being the proximal ring.) Each of electrical terminals 364 and 366 may be configured to flexibly contact a different one of the two conductive elements when the Luer male connector and the Luer female connector mate properly.

Another difference between the one-ring configuration of FIG. 2A and the two-ring configuration of FIG. 3A is that in the two-ring configuration, an electronic chip 305 is mechanically interposed between the two conductive rings and electrically powered (activated) via or by the conducting rings when the male and female Luer connectors are properly engaged. Electronic chip 305 may be retained in place between the two conductive rings, for example, by being attached or connected to them, or by being embedded in secondary male member 326.

Electronic chip 305 may include a memory in which data is or may be stored. Data stored in the memory may include, for example, information related to, for example: (1) an identification or serial number (ID) of the tube and/or of the connector and/or of a system that can be paired with the tube, (2) the class or type of the tube and/or of the connector and/or of a system that is in use, (3) the number of times that the tube was used, (4) an accumulated time that the tube was in use, etc.

Identifying the type, class or another property of, for example a tube (for example) by the medical system may enable the medical system (for example) to adjust various alarm settings and/or parameters that may have certain effects on the system (e.g., accuracy of measurement, signal rise time, system overall response time, etc.) associated, for example, with the medical system. For example, a tube may be designed for, or be classified as being suitable for, intubation applications or for non-intubation applications, or it may be designed for adult use or for pediatric use, etc., and the medical system may automatically recognizes these instances and adapt itself accordingly. The medical system (e.g., a capnography monitor) may be configured to, for example, set off an alarm indication if a system reading (e.g., $CO_2$ reading) is below or above an alarm threshold level, and the alarm threshold level may automatically be set by the system in advance per the type of, for example, the tube. Similarly, an operation parameter may be adjusted or compensated according to the tube type in order to increase the overall system's accuracy.

Electronic chip 305 may also include a controller. The controller may be configured to read (receive) data from an external system (e.g., medical system) and write the data into the memory, and to read (retrieve) data from the memory and send the read data to the external system. For example, each time the male and female Luer connectors are properly engaged, the controller may update a counter value which is stored in the memory, or a time value (e.g., 'timestamp') corresponding to, for example, the time period the male and female connectors are properly engaged, or the accumulated time the male and female connectors have been properly engaged.

Electronic chip 305 may also include a communication interface that the controller may use to communicate with an external system, for example, with a medical system (e.g., capnographic system), via communication terminal(s) or wires. For example, electronic chip 305 may use electrically conductive elements 370 and 380 and electrical terminals 364 and 366 as communication lines as well as power lines. Luer male connector 310 may include an electrical connector or socket 309 to which an electrical cable 311 may be connected.

Luer male connector 310 may include a void or recess 350 for accommodating (including or containing) a circuit board (e.g., printed circuit board—"PCB") 360. Circuit board 360 may receive an electric power from an external system (e.g., from a medical monitoring system) via electrical cable 311, and, while the male and female connectors are properly engaged, it may power up electronic chip 305 via terminals 364 and 366 and conductive rings 370 and 380.

Electronic chip 305 may communicate with the external system via electrical cable 311 by using any suitable communication protocol, for example the communication protocol I2C, which is typically used to connect peripheral Integrated Circuits ("ICs") to processors and microcontrollers. Upon proper engagement of the male and female connectors, and while the two connectors are properly engaged, electronic chip 305 may send data to the external system, and the external system may send data to electronic chip 305. For example, the external system may send to electronic chip 305 information representative of, or related to, the date and/or time on which the two connectors were properly connected, and/or the date and/or time of tube's filter occlusion, and/or a 'signature' (e.g., an ID, serial number or type) of the external system (e.g., a medical monitor), etc. In some embodiments, the external system may save information that electronic chip 305 sends to it, and the external system may evaluate the system or a component thereof, for example statistically, based on or using that information. In some embodiments, electronic chip 305 may save information that it receives from the external system during one medical procedure, and send it back to the external system. The external system may respond to the communication from electronic chip 305 by, for example, introducing to a user information that is related to the tube in use; for example that the tube has been used a maximum permitted number of times and it is, therefore, unusable. The external system may also respond to the communication from electronic chip 305 by, for example, sending updated data to electronic chip 305, and electronic chip 305 may respond to the communication by, for example, updating or replacing data in its memory.

Establishing communication between electronic chip 305 and the external system (e.g., via cable 311) is an indication to the external system that the male and female connectors are properly engaged. When this condition (proper engagement) is indicated, the external system may commence a medical procedure. For example, the external system may start receiving exhaled gas (e.g., $CO_2$) or output sedative drug through tube 302, etc.

Electronic chip 305 may include, for example, a switch whose state ("closed", "open") is controllable by the controller or, in the absence of a controller, by a voltage that is provided to chip 305 by the electric terminals 364 and 366 when the two Luer connectors properly mate. That is, when the male and female connectors are properly engaged, electronic chip 305 is powered up via terminals 364 and 366, the result of which is that the switch transitions from its 'open' state to its 'closed' state. Transitioning the switch to its 'closed' state causes a connector-mating indication (CMI) signal to be transferred via terminals 364 and 366, circuit board 360, wires 394 and 396 and cable 311, to the external system.

On circuit board 360 may optionally be mounted, for example, a CMI 362. CMI 362 may be or include, for example, one or more light sources (e.g., light emitting diodes—'LEDs'). The light source(s) mounted on circuit board 360 may be activated only when Luer male connector 310 and Luer female connector 320 mate properly; e.g., only when secondary male part 326 of primary female member 322 properly mates with secondary female part (void) 314 of primary male member 312. CMI 362 may be used to output an in-situ indication that the two connectors are engaged properly in response to a signal that CMI 362 may receive from electronic chip 305 or from the external system. The electrical schematic associated with Luer connector 300 is more fully described below in connection with, for example, FIGS. 3C-3D.

Light source 362 may be optically coupled to an optical fiber (not shown in FIG. 3A) via which a user may see a light that originates from the light source. Alternatively or additionally, the Luer male connector (310) may include an optical window 303 (an indication, or observation, window) through which light originating from light source 362 may be visible to the user.

When light source 362 (an example CMI) is activated, the light it emits may pass through observation window 303 in order for it to be observed, for example, by health care staff. Indication window 303 may be made of or include, for example, a plastic material that may be transparent or translucent to visible light. Alternatively, or additionally, the light that light source 362 emits may be transferred outside connector 310 (for example to an external monitoring system), or made visible to a health care person, via or through an optical fiber. Circuit board 360 may be, for example, ring shaped with a concentric through hole to enable insertion of tube 302 into Luer male connector 310 during assembly of Luer male connector 310.

Tube 302, which is connected to Luer male connector 310, has a fluid flow channel 318 that is in fluid flow connection with secondary female void 314. Tube 338, which is connected to Luer female connector 320, has a fluid flow channel 334 that is in fluid flow connection with a flow fluid channel 327 and fluid flow channel 336 in secondary male member 326. When Luer male connector 310 and Luer female connector 320 properly mate, all fluid flow channels form a continuous fluid flow channel.

Figure 3B:
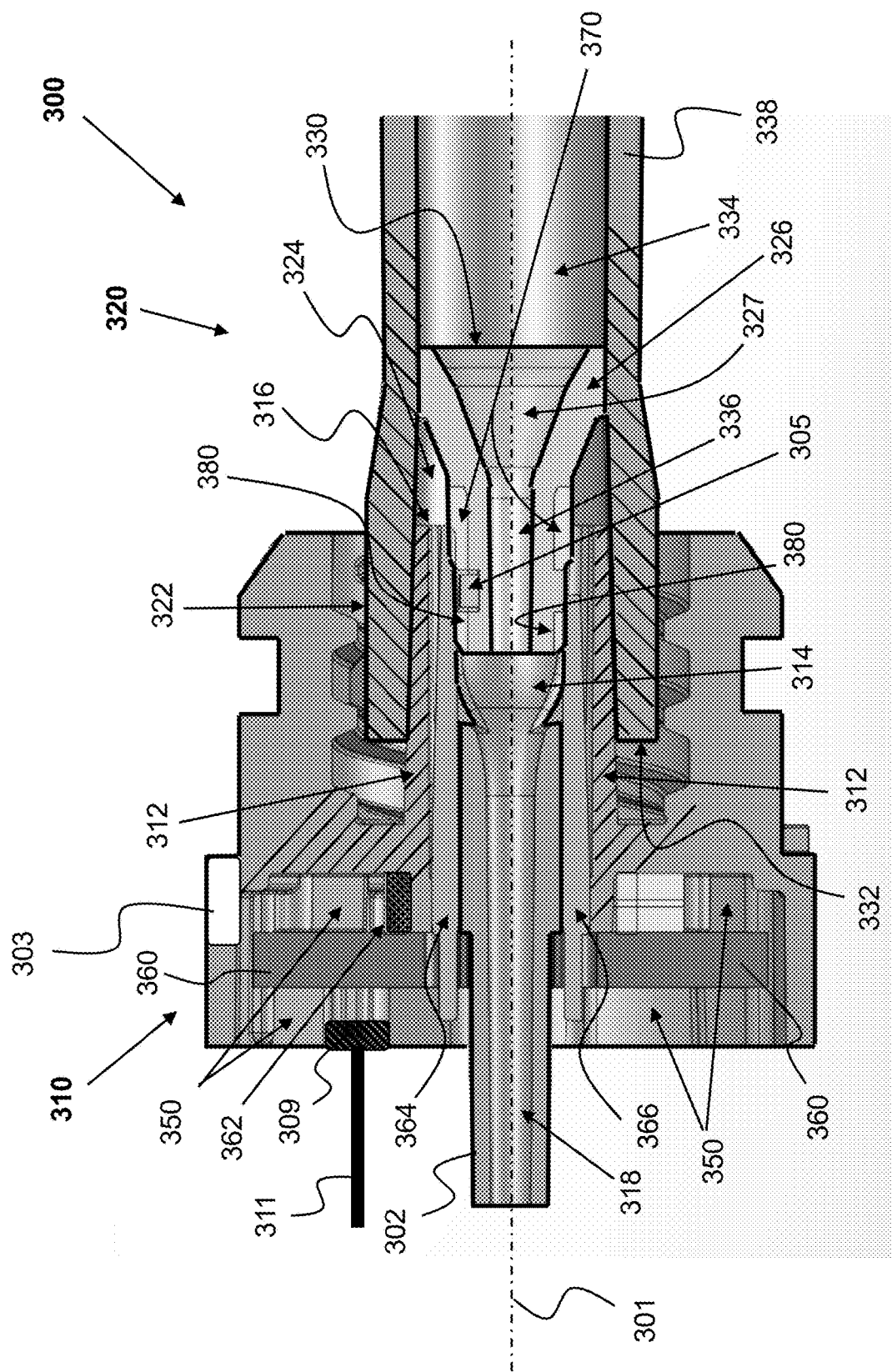
FIG. 3B shows a cross-sectional view of a two-ring Luer connector according to an example embodiment.

FIG. 3B depicts a cross-sectional view of a Luer connector 300 in connection with FIG. 3A. (A same reference numeral in FIGS. 3A-3B refer to a same or equivalent element.) Luer male connector 310 and Luer female connector 320 are properly engaged, therefore terminals 364 and 366 respectively touch (are in electrical connection with) proximal conductive ring 370 and distal conductive ring 380. In an electro-mechanical configuration that includes two conductive elements (for example conductive rings 370 and 380) and an electrical circuit (for example electronic chip 305) that is interposed between the two conductive elements, CMI 362 may be optional.

Figure 3C:
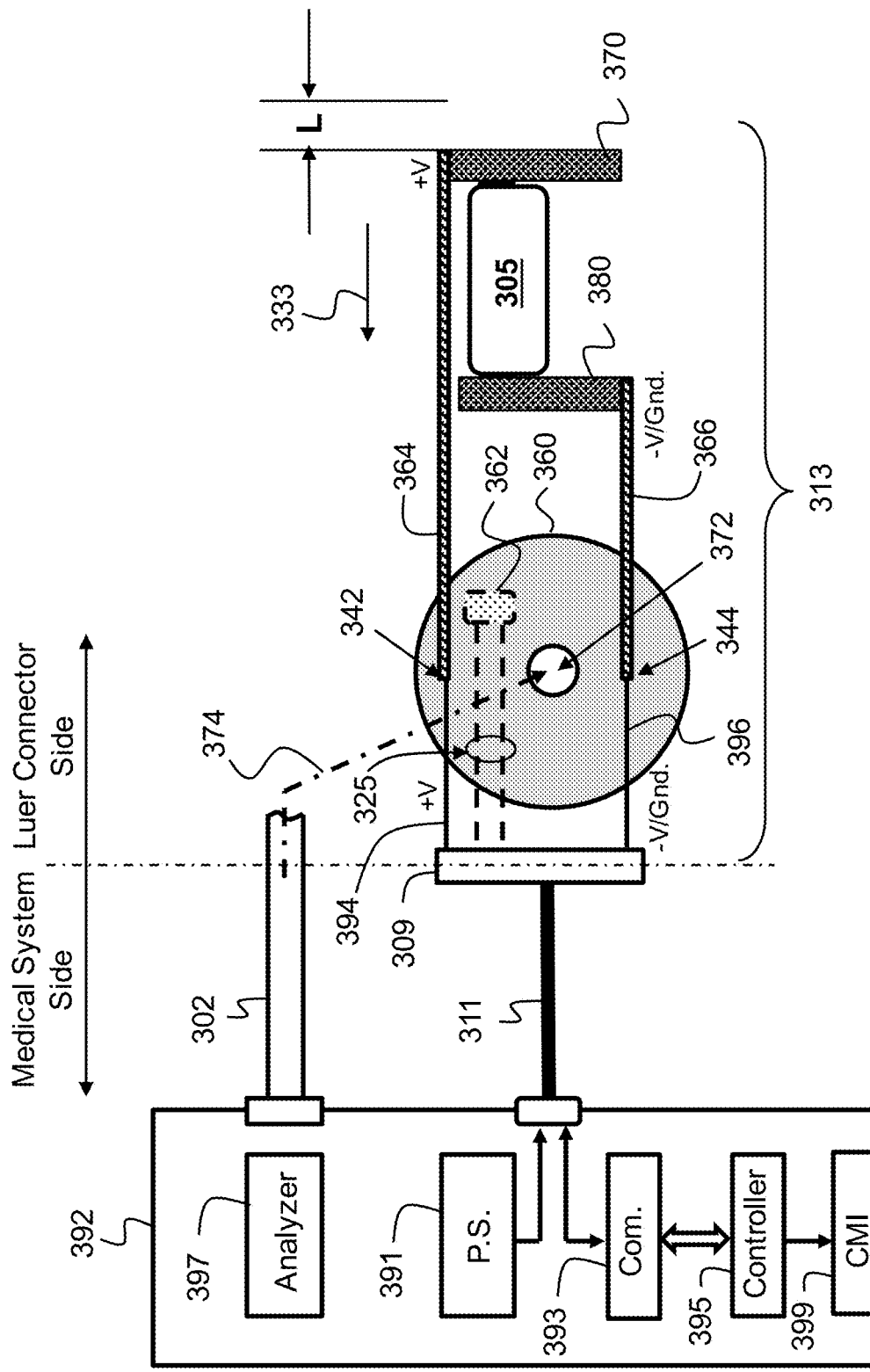
FIG. 3C schematically illustrates an example electrical circuit schematics of a two-ring Luer connector in engagement state according to an example embodiment.

FIG. 3C schematically illustrates an electrical circuit 313 associated with (representing) Luer connector 300 of FIG. 3A. To a medical system 392 may be connected flexible tube 302 through which medical system 392 may, depending on the system used, output or receive a fluid flow, for example of breathing gases. For example, system 392 may provide Oxygen to a patient through flexible tube 302, or measure/monitor the level of a patient's exhaled carbon dioxide. System 392 may use electrical cable 311, for example, to transfer electrical power from a power supply source 391 of system 392 to (power up) Luer connector's electric circuit 313, including electronic chip 305 (an example electronic circuit), that may use cable 311 to transfer signals or data to, and exchange information with, system 392.

Electrical cable 311 may have wires that are respectively connected, via port 309, to a '+V' wire 394 and to a '−V' (or ground, Gnd.) wire 396. Wires 394 and 396 may be connected to circuit board 360. Electrical terminals 364 and 366 may also be connected to (such as by being mounted on) circuit board 360 such that they are respectively connected, for example via circuit board 360, to wires 394 and 396. In the disengagement state, when Luer male connector 310 and Luer female connector 320 are not engaged or they are improperly engaged, terminal 364 and/or terminal 366 may respectively be disconnected from conductive rings 380 and 370 by a 'disengagement' gap L between each terminal and the respective ring. If a disengagement gap L exists between any terminal (e.g., terminal 364 or 366, or both terminals) and the pertinent ring(s), this 'breaks' the power supply circuit such that electronic chip 305 becomes or remains deactivated.

During insertion of Luer female connector 320 into Luer male connector 310, rings 370 and 380, with circuit board 305 mechanically and operationally 'sandwiched' between the rings and powered through them, move, en masse, in direction 333 together with Luer female connector 320. When proper engagement between the two Luer connectors is obtained, disengagement gap L is zeroed out, causing terminals 364 and 366 to respectively contact proximal ring 370 and distal ring 380. Circuit board 360 may be, for example, ring shaped (e.g., it may be rounded with concentric through hole 372) to enable insertion (374) there through of tube 302 into Luer male connector 310 during the Luer male connector assembly process.

When the Luer male connector and the Luer female connector are not properly engaged, conducting rings 370 and 380 do not touch terminals 364 and 366 and, therefore, they do not receive power from power supply source 391 of medical system 392. During mating of the Luer male connector and the Luer female connector, disengagement gap L initially exist between the two parts, but it narrows down as the two connectors near proper mating. When the Luer male connector and the Luer female connector are properly engaged, disengagement gap L is zeroed out, in which case terminals 364 and 366 are respectively connected to conducting rings 370 and 380. As a result of the connection between the terminals and the rings, power supply 391 (through cable 311, wires 394 and 396, terminals 364 and 366 and rings 370 and 380) powers up electronic chip 305. (Electronic chip 305 is fixedly interposed ('sandwiched') between conducting rings 382 and 384, and is always in electrical connection with the rings.)

When electronic chip 305 is electrically powered, it may initiate communication with a controller 395 of medical system 392 via communication driver or interface 393 of medical system 392. When communication is established, via communication driver or interface 393, between controller 395 of medical system 392 and electronic chip 305, controller 395 interprets the on-going communication as an indication that the Luer male connector and the Luer female connector have mated properly. During a communication session, electronic chip 305 may send to controller 395 various types of data that are stored in a memory of electronic chip 305. For example, electronic chip 305 may send to controller 395 information related to the identification (ID) of electronic chip 305 and/or information related to the tube and connector, for example the tube class, connector type and/or serial number, the accumulated time the tube was used, the number of times the tube was used, etc. Controller 395 may use information that electronic chip 305 sends to it to determine (e.g., based on a class of the tube) whether the tube is for general use or for a specific use. Specific use may refer to, for example, using a tube in children or in adults, or in people connected to a respiratory machine (or other life-supporting system), etc. Controller 395 may operate a pump and analyzer of system 392 according to, for example, the class of the tube.

When system 392 (e.g., controller 395) determines that the Luer male (e.g., 310) and female (e.g., 320) connectors are engaged properly, system 392 (e.g., controller 395) may commence a predetermined medical procedure. For example, controller 395 may activate a pump in order for analyzer 397 to receive gas samples, for example exhaled carbon dioxide, via tube 302, and control analyzer 397 to concurrently analyze or monitor the gas inflow.

System 392 (e.g., controller 395) may determine that the Luer male and female connectors are engaged properly based on the existence of successful communication with electronic chip 305. That is, if system 392 determines, for example by using a communication timeout mechanism or a communication error mechanism, that the communication with electronic chip 305 is continuous; that is, if there are no communication gaps or the number of gaps is smaller than a predetermined threshold value (and therefore negligible), system 392 determines that the involved Luer connectors are properly engaged. In other words, a sustained communication between system 392 and electronic chip 305 is used as an indication to proper mating of the two connectors. In some embodiments, the communication timeout setting may be adjustable. For example, it may be adjusted to suit the medical procedure involved. (It may be that different medical procedures may require different communication timeout settings.) System 392 may be designed to apply a communication timeout setting according to the involved medical procedure. System 392 may use an initial communication timeout setting and change it later based on data that it receives from electronic chip 305.

When system 392 detects proper mating between Luer male connector 310 and Luer female connector 320, system 392 (e.g., controller 395) may output a connection indication signal to a CMI 399 on-board system 392 to indicate (e.g., visually, audibly, etc.) the proper connector mating, for example to the system operator, healthcare personnel or technician. Alternatively, or additionally, controller 395 may send a connection indication signal, via cable 311 and wires 325, to a second CMI (CMI 362) that is mounted on circuit board 360, to provide an in-situ indication of proper mating of the Luer male and Luer female connectors. Each of CMI 399 and CMI 362 may be or include, for example, a light source (e.g., LED), an electric buzzer, an electromechanical vibrator, etc. Communication between electronic chip 305 and communication driver or interface 393 of medical system 392 may be performed via electric terminals 364 and 366. That is, electric terminals 364 and 366 may be used both as the electronic chip 305's power lines and communication lines.

Figure 3D:
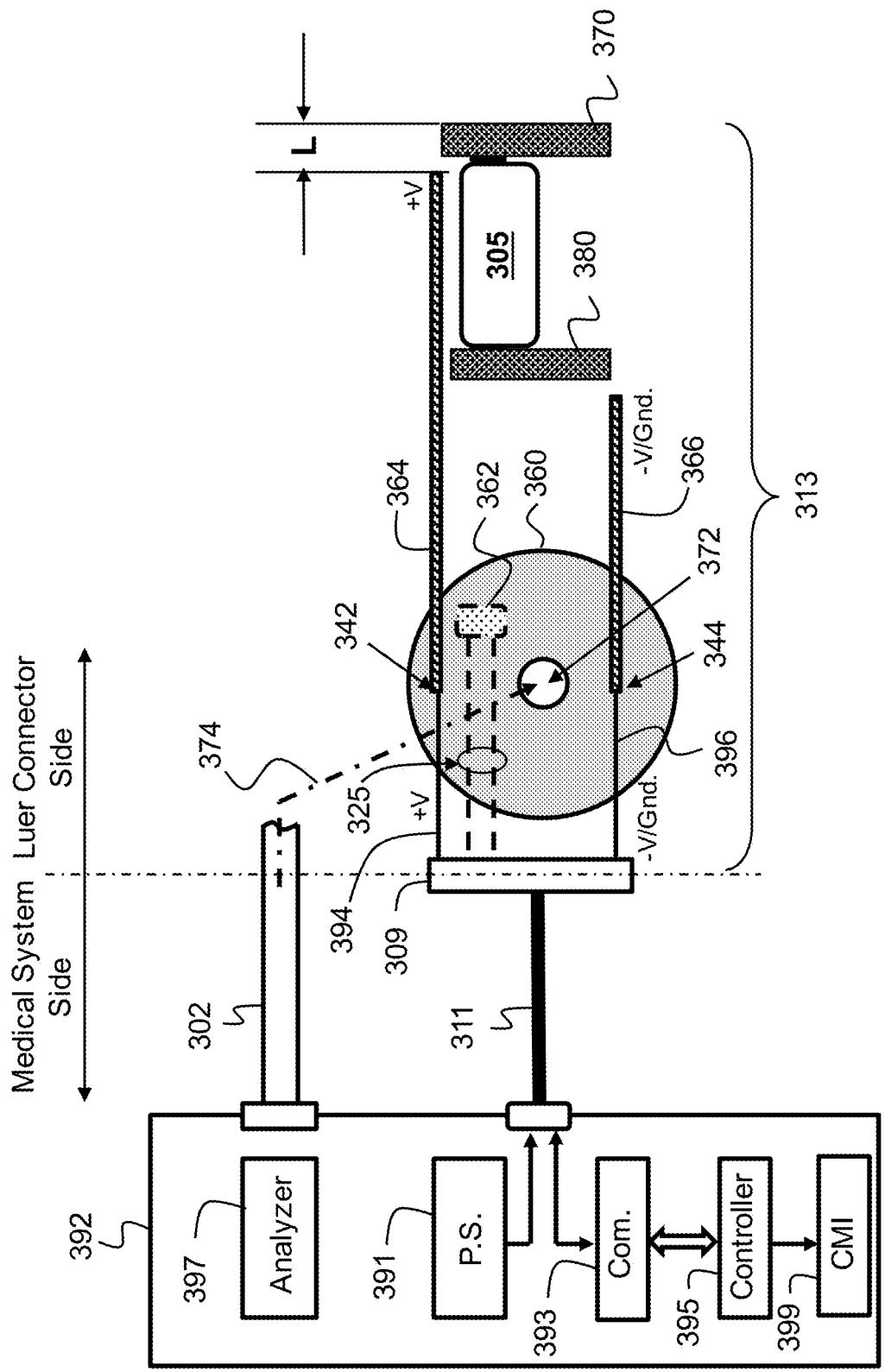
FIG. 3D schematically illustrates the electrical circuit schematics of FIG. 3C in disengagement state.

FIG. 3D shows electrical schematic 313 of a Luer connector in a disengagement state where electric terminals 364 and 366 are, respectively, symbolically shown as disengaged from conducting elements 370 and 380.

FIG. 4A shows another type of connection indicator (a tactile connection indicator 400) for a Luer connector according to an example embodiment. Tactile connection indicator 400 has a first side that has a flat and relatively smooth surface 440, and a second side or 'friction side' 450 that has a 'friction surface'. Tactile connection indicator 400 may be a rounded, ring-shaped, flat object (e.g., disc) 410 having an external diameter D1 and an inner diameter D2 of an opening (a through hole) 420. Ring-shaped object's friction side includes, for example, a plurality of convex projections (e.g., rounded projections, dome like projections, curved projections, humps, etc.) that are circumferentially located on the friction side. Some of the plurality of convex projections are shown at 430. (Ring-shaped object 410 and friction projections 430 may be manufactured as one object, or they can be manufactured separately and, then, joined.) The convex projections may be evenly (or unevenly) spaced around a center 402 point of rounded tactile connection indicator 400. FIG. 4B shows a cross-sectional side view of the tactile connection indicator 400 of FIG. 4A.

FIG. 4C depicts a cross-sectional view of a Luer male connector 460 and the location of the tactile connection indicator 400 of FIGS. 4A-4B in Luer male connector 460. To Luer male connector 460 may be connected a tube 470 whose distal part 480 may be mechanically secured inside Luer male connector 460. (Distal part 480 of tube 470 is, or forms, a 'primary male' part of Luer male connector 460, hence the term 'Luer male connector'.)

Primary male part 480 of Luer male connector 460 has a diameter D3. Opening 420 (inner diameter D2 of tactile connection indicator 400) is slightly larger than diameter D3 of primary male part 480, so that, during assembling of connector 460, primary male part 480 can be inserted through opening 420 of ring-shaped object 410, or ring-shaped object 410 can be mounted on Luer male connector 460 through insertion of primary male part 480 through opening 420 of ring-shaped object 410. Luer male connector 460 has a screwing thread 466 (a raised helical rib) with an external diameter D4. Diameter D4 is slightly larger than the external diameter (D1) of ring-shaped object 410, so that ring-shaped object 410 can be accommodated in connector 460. Ring-shaped object 410 may be mounted in Luer male connector 460 by being screwed all the way through, from distal end 490 of primary male part 480 to proximal end 492 of primary male part 480, until a protrusion or wall 494 in Luer male connector 460 mechanically inhibits further movement of ring-shaped object 410. Luer male connector 460 includes a connector base 452, and primary male member 480 extends distally (in direction 464) from connector base 452, towards a Luer female connector insertion opening 456 of Luer male connector 460.

When tactile connection indicator 400 is mounted in Luer male connector 460, the smooth side (side 440) of tactile connection indicator 400 faces rearward (462), towards tube insertion opening 454 of tube 470 into the connector, and the friction surface (side 450) of tactile connection indicator 400 faces forward (in the opposite direction 464), towards a Luer female connector insertion opening 456 of the Luer male connector from which the Luer female connector enters (engages with) the Luer male connector.

A primary female member of a Luer female connector may have, on its distal end, a plurality of concave recesses, a concave recess for accommodating one of convex friction projections 430. To engage the Luer female connector with Luer male connector 460, the primary female member of the Luer female connector is to be screwed into Luer male connector 460 until the distal end of the primary female member of the Luer female connector touches convex friction projections 430. When this occurs, the primary female member of the Luer female connector is to be rotated slightly further until all convex projections 430 in Luer male connector 460 respectively occupy (enter) the concave recesses in the primary female member, for example with a 'click'. To enable click insertion of convex friction projections 430 into the concave recesses, the multiple projections 430 of tactile connection indicator 400 may be made flexible, or they may be retractable using, for example, coil springs. Making convex projections 430 retractable enables them to retreat in order to enable the extra rotation of one connector with respect to the other, which is required to align the concave recesses of the primary female member of a Luer female connector to the convex projections of tactile connection indicator 400. (The extra rotation mechanically pushes back the projections 430 from their initial 'bulging' state, and projections 430 protrude again (resume their initial bulging state), into the concave recesses, when the convex protrusions are respectively aligned with the concave recesses in the primary female member. Proper engagement of the Luer male connector and Luer female connector is, therefore, indicated when a 'light' mechanical resistance to engagement is felt at first, and, after some additional (the extra) rotation of, for example, the Luer female connector, the resistance decreases until each of convex projections 430 completely engages (fully occupies) the respective concave recess. When the convex protrusions of the Luer male connector are fully aligned with the concave recesses of the Luer female connector, a larger 'friction' may be felt if one of the connectors (thus its convex protrusions or concave recesses, depending on the connector) is rotated out of alignment with respect to the other connector (thus with respect with its concave recesses or convex protrusions, depending on the other connector).

FIG. 5 depicts a cross-sectional view of a Luer male connector 500 according to another embodiment. Luer male connector 500 may include a connector base 506, a screwing thread 502 and a primary male member 580 that extends distally from connector base 506, is internally concentric to screwing thread 502 and includes a concentric secondary Luer female member 508 having a female void 508'.

Luer male connector 500 may also include a micro switch 510 that is retained in Luer male connector 500 and configured to transition micro switch 510 from an 'open' state of the switch to a 'closed' state of the switch when Luer male connector 500 and a Luer female connector properly mate with one another. Micro switch 510 may reside or be accommodated in a space between (defined by) screwing thread 502 and primary Luer male member 580. (In this embodiment, primary Luer male member 580 is a distal part of a tube 570.) In this embodiment, Luer male connector 500 micro switch 510 is used to indicate proper engagement between Luer male connector 500 and a Luer female connector.

In some embodiments, Luer male connector 500 may include a circuit board 520 that may be similar to, for example, circuit board 260 (FIG. 2A) or to circuit board 360 (FIG. 3A), and micro switch 510 may be mounted on circuit board 520. Micro switch 510 (a normally open 'limit' switch) may include a pin plunger (512) as an actuator, to be actuated by a secondary male member of a Luer female connector to transition micro switch 510 from the 'open' state of the micro switch to the 'closed' state in which the switch outputs an electrical signal indicative of proper mating of or between the Luer male connector (500) and the Luer female connector. Circuit board 520 may be ring shaped to enable through-passage of tube 570, and it may be accommodated in a base void 550 in connector base 506.

Micro switch 510 may extend from circuit board 520 forwardly, towards a distal end 590 of primary male member 580. Screwing thread 502 of Luer male connector 500 has an internal diameter D5 that is larger than the external diameter (D6) of primary male member 580 and defines therewith a 'rounded' open space 504 which is spacious enough to accommodate micro switch 510, or part thereof. Open space 504 is spacious enough to accommodate also a primary female member of a Luer female connector. Micro switch 510 may receive an electrical signal from, and, in response to it being actuated by a Luer female connector, return the signal as a feedback signal to an on-board circuit (a circuit in Luer male connector; e.g., circuit board 520), or to an external system (e.g., system 292 or system 392) in a similar way as described in connection with, for example, FIG. 2B. In some other embodiments, micro switch 510 may be mounted or embedded in Luer male connector 500 'directly'; that is, without requiring circuit board 520. (Micro switch 510 may be operationally retained or embedded, for example, in a niche in Luer male connector 500.)

To engage the Luer female connector with Luer male connector 500, the primary female member of the Luer female connector is to be screwed into Luer male connector 500 until the distal end of the primary female member of the Luer female connector actuates pin plunger 512 of micro switch 510. When Luer male connector 500 and the Luer female connector engage properly, pin plunger 512 is actuated (by the primary female part of the Luer female connector), causing the switch to transition to the 'closed' state in which the switch returns an electrical feedback signal to an on-board circuit, or to an external system. The on-board circuit (520) or external system may, then, indicate to a user, for example visually and/or audibly, that the two Luer connectors are properly mate with one another. Alternatively or additionally, circuit board 520 may include a light source, an electric vibrator, a buzzer, etc. to provide to the user an in-situ indication regarding proper engagement of the Luer male connector and the Luer female connector.

Various aspects of the various embodiments disclosed herein are combinable with the other embodiments disclosed herein. Although portions of the discussion herein may relate to one or two rings and to specific circuit boards, embodiments of the invention are not limited in this regard and may include, for example, the connection indicator may be embedded (adapted to be used in or by) various types of Luer connection systems, and other numbers of rings and different types of circuit boards may be used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A Luer connector system, comprising:
   a Luer male connector for a Luer female connector, the Luer male connector comprising:
   a connector base, said connector base having a base void;
   a primary male member extending distally, in a first direction, from the connector base, said primary male member including a concentric secondary female member having a female void;
   a first elongated electrical terminal and a second elongated electrical terminal, the first and second elongated electrical terminals extending along a length of the Luer male connector; and
   a connection indicator,
   wherein the first and second elongated electrical terminals are electrically connected to the connection indicator and are configured to electrically attach to a conductive element that is mounted on a secondary male member of a Luer female connector in order to power up the connection indicator to indicate when the Luer male connector and the Luer female connector mate properly;
   wherein the conductive element mounted on the secondary male member comprises two axially spaced apart conductive rings connected to an electrical circuit comprising a controller,
   wherein the controller is configured to communicate with an external system via the two conductive rings and via the first and second elongated electrical terminals.

2. The Luer connector system as in claim 1, wherein the Luer male connector comprises the connection indicator, said connection indicator comprises a device selected from the group consisting of: a light source, a sound making device and an electromechanical vibrator.

3. The Luer connector system as in claim 2, wherein the light source is optically coupled to an optical fiber.

4. The Luer connector system as in claim 2, wherein the Luer male connector further comprises an optical window through which light originating from the light source is visible.

5. The Luer connector system as in claim 1, wherein the connection indicator resides in said base void.

6. The Luer connector system as in claim 1, wherein the base void comprises a circuit board, wherein the first elongated electrical terminal, second elongated electrical terminal and the connection indicator are mounted on said circuit board.

7. The Luer male connector as in claim 6, wherein each of the first and second electrical terminals has a proximal end and a distal end, each proximal end is mounted on the circuit board and each distal end extends in the first direction into the female void of the secondary female member, wherein the connection indicator is configured to be powered up via the circuit board, via the first and second electrical terminals, and via the conductive element mounted on the secondary male member of the Luer female connector when the Luer male connector and the Luer female connector mate properly.

8. The Luer connector system as in claim 6, wherein the circuit board is ring shaped to enable passage there through of a tube.

9. The Luer connector system as in claim 1, wherein the first and second electrical terminals are pre-conditioned to flex by the conductive element mounted on the secondary male member of the Luer female connector when the Luer male connector and the Luer female connector mate properly.

10. The Luer connector system as in claim 1, wherein each of the first and second electrical terminals is configured to flexibly contact one of the two conductive rings when the Luer male connector and the Luer female connector mate properly.

11. The Luer connector system as in claim 1, wherein the connection indicator is or resides in an electrical circuit, said electrical circuit interposed between the two conductive rings and configured to be powered via the two conductive rings and first and second electrical terminals when the Luer male connector and the Luer female connector properly mate.

12. The Luer connector system as in claim 1, wherein the electrical circuit comprises the controller, a communication interface and a memory.

13. The Luer connector system as in claim 12, wherein the controller is configured to exchange data with the external system via the communication interface when the Luer male connector and the Luer female connector properly mate.

14. The Luer connector system as in claim 13, wherein the external system is configured to detect proper mating of the Luer male connector and the Luer female connector through communication with the controller.

15. A Luer connector system, comprising:
a Luer male connector for a Luer female connector, the Luer male connector comprising:
a connector base, said connector base having a base void;
a primary male member extending distally, in a first direction, from the connector base, said primary male member including a concentric secondary female member having a female void;
a first elongated electrical terminal and a second elongated electrical terminal, the first and second elongated electrical terminals extending along a length of the Luer male connector; and
a connection indicator,
wherein the first and second elongated electrical terminals are electrically connected to the connection indicator and are configured to electrically attach to a conductive element that is mounted on a secondary male member of a Luer female connector in order to power up the connection indicator to indicate when the Luer male connector and the Luer female connector mate properly;
wherein the connection indicator is or resides in an electrical circuit that comprises a controller, a communication interface and a memory,
wherein the controller is configured to exchange data with an external system via the communication interface, and
wherein the data includes data selected from the group consisting of: (i) data related to an identification (ID) of a tube connected to the Luer male connector, (ii) data related to the Luer male connector or to a system that can use the tube or Luer connector system, (iii) data related to a class or type of the tube that is in use, (iv) data related to a number of times that the tube was used, and (v) data related to an accumulated time that the tube was in use.

16. The Luer connector system as in claim 15, wherein the external system adjusts an alarm setting or a parameter based on the data.

17. A Luer connector system, comprising:
a Luer male connector for a Luer female connector, the Luer male connector comprising:
a connector base, said connector base having a base void;
a primary male member extending distally, in a first direction, from the connector base, said primary male member including a concentric secondary female member having a female void;
a first elongated electrical terminal and a second elongated electrical terminal, the first and second elongated electrical terminals extending along a length of the Luer male connector; and
a connection indicator,
wherein the first and second elongated electrical terminals are electrically connected to the connection indicator and are configured to electrically attach to a conductive element that is mounted on a secondary male member of a Luer female connector in order to power up the connection indicator to indicate when the Luer male connector and the Luer female connector mate properly;
wherein the connection indicator is or resides in an electrical circuit that comprises a controller, a communication interface and a memory,
wherein the controller is configured to exchange data with an external system via the communication interface,
wherein the external system is configured to detect proper mating of the Luer male connector and the Luer female connector through communication with the controller, and
wherein the base void comprises a circuit board, on said circuit board is mounted a second connection indicator, wherein the external system is configured to output a connection indication signal to the second connection indicator when the external system detects proper mating of the Luer male connector and the Luer female connector.

18. A Luer female connector for a Luer male connector, the Luer female connector comprising:
a primary female member configured to mate with a primary male member of the Luer male connector;
a secondary male member concentrically formed in said primary female member, the secondary male member configured to mate with a secondary female member of the Luer male connector;
two conductive elements, the two conductive elements axially spaced apart on the secondary male member along a lengthwise axis of the secondary male connector; and
wherein the conductive elements are connected to an electrical circuit comprising a controller,
wherein the controller is configured to communicate with an external system via the two conductive elements on the secondary male member when the Luer female connector and the Luer male connector properly mate.

19. The Luer female connector as in claim 18, wherein the electrical circuit comprises the controller, a communication interface and a memory.

20. A Luer male connector comprising:
a Luer male connector body including an internal screwing thread;
a primary male member extending distally from a connector base of the Luer male connector body, the primary male member internally concentric to the screwing thread; and
a connection indicator mounted between the screwing thread and the primary male member, the connection indicator comprising a first side and a second side having a friction surface,
wherein the first side and the friction surface of the connection indicator respectively face a tube insertion opening and a Luer female connector insertion opening of the Luer male connector.

21. The Luer male connector as in claim 20, wherein the connection indicator comprises a plurality of convex friction projections, the plurality of convex friction projections configured to respectively occupy a plurality of concave recesses in a primary female member of a Luer female connector when the Luer male connector and the Luer female connector mate properly.

22. The Luer male connector as in claim 21, wherein a tactile indication regarding proper mating of the Luer male connector and the Luer female connector is indicated by the connection indicator when the plurality of convex friction projections respectively occupy the plurality of concave recesses.

23. A Luer male connector, comprising:
a Luer male connector body including a connector base including a base void;
a circuit board residing in the base void;
a screwing thread on an interior portion of the Luer male connector body;
a primary male member extending distally from the connector base and internally concentric to the screwing thread; and
a switch, said switch mounted on the circuit board and residing between the screwing thread and the primary male member, the switch configured to transition from an open state of the switch to a closed state of the switch when the Luer male connector and a Luer female connector properly mate.

24. The Luer male connector as in claim 23, wherein the switch comprises a pin plunger actuatable by a primary female member of the Luer female connector to transition the switch to the closed state in which the switch outputs an electrical signal indicative of proper mating of the Luer male connector and the Luer female connector.

25. The Luer connector system as in claim 23, wherein the circuit board is ring shaped to enable through-passage of a tube.

* * * * *